United States Patent [19]

Smith

[11] 4,436,718

[45] Mar. 13, 1984

[54] IODINATING REAGENT

[75] Inventor: Paul K. Smith, Roscoe, Ill.

[73] Assignee: Pierce Chemical Company, Rockford, Ill.

[21] Appl. No.: 311,077

[22] Filed: Oct. 13, 1981

[51] Int. Cl.$^3$ .................. A61K 43/00; A61K 49/00
[52] U.S. Cl. .......................... 424/1.1; 424/9; 428/407; 521/25; 252/645
[58] Field of Search .............. 424/1, 1.5, 9; 428/407; 521/25; 252/645

[56] References Cited

U.S. PATENT DOCUMENTS

| | | | |
|---|---|---|---|
| 3,886,080 | 5/1975 | Schucker et al. | 521/25 |
| 3,954,411 | 5/1976 | Snyder | 422/71 |
| 4,010,250 | 3/1977 | Parikh et al. | 424/1 |
| 4,115,540 | 9/1978 | Digenis et al. | 424/1 |
| 4,272,503 | 6/1981 | Camin et al. | 424/1 |
| 4,290,965 | 9/1981 | Stöckin et al. | 424/1 |
| 4,305,922 | 12/1981 | Rhodes | 424/1 |

FOREIGN PATENT DOCUMENTS 2523793  12/1975  Fed. Rep. of Germany ........ 521/25

*Primary Examiner*—Christine M. Nucker

[57] ABSTRACT

An improved oxidant useful in mediating the iodination of biological specimens containing tyrosyl or synthetically incorporated phenolic residues is disclosed. The oxidant is water insoluble, is easy to handle, and can be prepared with a determinable oxidizing capacity. An illustrated oxidant is a polystyrene bead having covalently attached to its surface N-chlorobenzenesulfonamide groups.

13 Claims, No Drawings

IODINATING REAGENT

This invention relates to the iodination of biological specimens and, more particularly, to a new oxidant which is useful in mediating iodination reactions, especially the radioiodination of proteins and peptides.

Radioactive labelling, usually with radioactive iodine (I*), of biological specimens is an important technique in a number of biochemical applications. Such applications include diagnostic procedures based on radioimmunoassay, membrane and cell receptor studies, and conformation studies of proteins and peptides.

Because of the presence of the amino acid, tyrosine, in most biological specimens and the facile reaction of I* with the phenolic moiety of tyrosine, radioiodination of the tyrosyl residue is the usual method of choice where radioactive labelling is to be employed. However, because of the extreme volatility of free I*, it is usually generated in situ from its sodium salt in the presence of an oxidant. N-chloro-4 methylbenzenesulfonamide, commonly referred to as chloramine-T, has for a number of years been used as the oxidant to mediate iodination reactions.

However, the use of chloramine-T has drawbacks. The reagent itself is harsh on many biological specimens. Moreover, in order to terminate iodinations using this water soluble oxidant the addition of a reducing agent is necessary. The most commonly used reducing agent is sodium metabisulfite and, as with chloramine-T itself, this compound frequently damages specimens.

Accordingly, water insoluble reagents are now commonly used as oxidants to mediate iodinations. With such, the in-situ generation of I* from sodium iodide, and, in turn, the iodination reaction can be easily stopped by physically separating the insoluble oxidant from the aqueous iodinating medium containing the iodinated specimen.

One popular water insoluble reagent used as an oxidant is 1, 3, 4, 6-tetrachloro-3α,6α-diphenylglycouril. This reagent, as with chloramine-T, is a chloramine, i.e., it contains the

group; but it is only sparingly soluble in water and can be used under mild conditions so as not to adversely affect the molecule being iodinated. As generally used, the reagent is plated onto a portion of the surface of the iodinating vessel. Since the reagent remains on the vessel surface, termination of the reaction occurs when the iodinated specimen is removed from the vessel by pouring or pipetting. Plating is effected by deposition out of an organic solvent solution of the chloramine reagent. While the reagent is quite useful, plating of reaction vessels is tedious and not very reproducible in achieving the same iodinating capacity, vessel to vessel. In addition, the reagent tends to solubilize in the presence of detergents which may be present in combination with the specimen being iodinated.

Another insoluble reagent is the enzyme, lactoperoxidase, which in use is immobilized on agarose. This enzyme catalyzes the iodination of proteins. However, its utility is limited by its inability to effectively function in the presence of high salt, some protein denaturing agents, or hemoprotein inhibitors such as azide, cyanide, or fluoride. Also, since the enzyme is a protein, it becomes iodinated itself, thus using up radioactive iodide reagent and creating disposal problems.

Now, however, in accordance with the present invention there is provided an improved oxidant useful in mediating the iodination of biological specimens containing tyrosyl or synthetically incorporated phenolic residues. Among other attributes the oxidant is water insoluble even in the presence of detergents and is easy to handle.

The oxidant of this invention comprises a water insoluble bead having covalently attached to its surface a plurality of molecules containing a chloramine group. An important characteristic of the oxidant is that the size and shape of the bead is compatible with easy physical separation of the oxidant from a solution of biological specimen to thereby permit termination of the oxidation reaction and, in turn, iodination, when desired.

The oxidant of this invention can be prepared by chemically treating commercially available beads to modify their surfaces to contain the necessary chloramine groups which, preferably are N-chloroarylsulfonamide groups because of stability. For example, if nylon beads are employed, N-chlorosulfonamide groups can be created by reacting endogenous and/or derived amine groups on the bead surface with benzene di-sulfonyl chloride followed by treatment with aqueous ammonia and then alkaline hypochlorite solution. The same reaction treatment can be used with beads fashioned from alkylamine substituted ceramic supports such as glass, alumina, silica, etc. With respect to aromatic containing polymers, such as polystyrene, the basic polymer backbone can be used to provide the desired aryl functionality. Thus, sequential treatment of polystyrene with chlorosulfonic acid, aqueous ammonia, and sodium hypochlorite yields the most preferred N-chlorobenzenesulfonamide functionality which can be structurally represented as

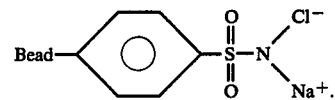

Iodinations are frequently done on small samples of biological specimens which may have taken days or weeks to obtain. Therefore, in accordance with a preferred embodiment of this invention, the bead has in addition to the above identified features, certain other physical and chemical characteristics. One of these is that it be non-porous. With a non-porous bead, the likelihood of loss of precious specimen through entrapment or entrainment within the bead is avoided. A similar consideration governs the selection of the chemical nature of the bead. It should not have surface characteristics whereby there is an affinity interaction between the specimen and bead. Non-porous beads fashioned from non-ionic polymers such as polystyrene have been found to be very suitable for use in this invention.

Bead size is an important parameter. The bead must be large eough so that it can be handled in a manner such that a known quantity can be added to a biological specimen and such that an easy separation of the specimen from the bead can be achieved. Beads of a size which can be individually handled with tweezers and which have dimensions such that they cannot be drawn up with iodinated specimen by, for example, an 18 gauge syringe needle, are useful.

The maximum size of the bead is influenced by the size of the sample to be iodinated and by how many beads are to be used at once. For iodinating efficiency, the bead should be submerged in the specimen being iodinated and, for a given volume of beads, greater capacity is obtained by using more, smaller beads rather than fewer, larger beads. So that a small quantity of oxidant can be employed for most iodinations, oxidation capacity should be at least 1 $\mu$eq/in$^2$ of bead surface area and, preferably, at least 10 $\mu$eq/inch$^2$. While bead shape is not especially important, useful oxidants can be prepared from spherical beads having diameters of about 0.01 inch to about 0.25 inch.

Though actual bead size and shape are not especially critical, it is preferred that size and shape be reproducible so that a plurality of beads with substantially identical size and shape can be obtained. In turn, by chemically treating at one time a batch of such beads to contain the necessary chloramine groups, beads with the same iodinating capacity will be obtained. And, by using one or several of the beads in a controlled oxidation experiment, the oxidizing capacity of those beads and, in turn, each of the beads in the batch can be determined. Where beads of different sizes or shapes are treated at once, or the beads are porous, then actual capacity is not as easily determinable since surface area of both the oxidant used in the control and of that used in the iodination must be measured or approximated.

EXAMPLE I

About 500 commercially available (Clifton Plastics, Clifton Heights, PA) non-crosslinked, non-porous polystyrene spherical beads (0.125 inch diameter) were placed in a flask containing 25 ml of chlorosulfonic acid (100%). After about three minutes, excess acid was drained off and the beads quenched in 200 ml ice and 100 ml water and then washed with water at a temperature just above freezing. Then, the beads were transferred to a flask containing 100 ml of ice and 100 ml of conc. ammonium hydroxide and, after about five minutes, removed and washed with water. Finally, the beads were added to 100 ml of commercial bleach and, after five minutes, washed with a solution of sodium bicarbonate and then blotted dry.

Oxidizing capacity can be determined by measuring how much of a known reductant is removed by a given amount of oxidant. Accordingly, 20 beads of oxidant prepared as above described are placed in a test tube with 2.00 ml of the reductant sodium thiosulfate (0.0100 N, $\mu$20 eq.) and 2.00 ml of pH 7.4 buffer (0.25 M sodium phosphate). After agitation for 50 minutes in an ultrasonic bath, the beads were removed and the liquid titrated with 0.0110 N. iodine solution to determine the amount of unreacted sodium thiosulfate. 0.89 ml of iodine solution was used (8.9 $\mu$eq. of I$_2$) meaning that 1.11 ml (11.1 $\mu$eq) of thiosulfate was consumed. In turn, this 11.1 $\mu$eq. is the oxidizing capacity of the 20 beads with each bead thus having a capacity of 0.55 $\mu$eq. Based on bead surface area, the oxidizing capacity is 11.2 $\mu$eq/in$^2$. This capacity is maintained for at least 6 months when the beads are refrigerated.

The following example illustrates the use of the oxidant prepared in Example I in mediating the iodination of a biological specimen. In Example II, PBS refers to a phosphate buffered saline without divalent cations which consists of 0.8% NaCl, 0.02% KCl, 0.215% Na$_2$HPO$_4$.7H$_2$O, and 0.02% KH$_2$PO$_4$ at pH7.2.

EXAMPLE II

100 $\mu$g of guinea pig anti-porcine insulin antiserum in 0.5 ml PBS was placed in a 5 ml capacity polystyrene reaction tube along with 1 mCi of Na$^{125}$I. One bead of oxidant, after having been washed twice with PBS (1 ml each wash), was added to the tube to initiate the iodination reaction which was then allowed to proceed for 15 minutes at room temperature (22° C.). The iodinated antiserum was then transferred with a Pasteur pipette to a second tube leaving the bead in the reaction tube. To maximize recovery of product, the bead was washed twice with 1.0 ml of PBS and the washings added to the second tube. Carrier iodide (0.5 $\mu$moles) was then added to the second tube to facilitate the removal of unreacted radioiodide by acid precipitation or gel filtration and as a safety precaution.

To determine specific activity of iodinated antiserum, carrier protein (8 ml of 0.1% (w/w) bovine serum albumin in ice-cold PBS) was first mixed with the iodinated antiserum in order to facilitate subsequent manipulations. Then cold trichloroacetic acid was added to a final concentration of 20% (w/v). The suspension was centrifuged for 10 min at 1500$\times$g at 4° C. and the pallet resuspended and washed three times with cold 20% trichloroacetic acid. The final pellet was solubilized in 10 ml of 0.1 N NaOH and a 10 $\mu$l aliquot counted in a Packard gamma scintillation spectrometer. Counting efficiency was determined by an iodine-125 gamma ray standard as 64%.

Specific activity of the iodinated antiserum was 3.5$\mu$Ci/$\mu$g. Moreover, about 95% of the original amount of antiserum was recovered and about 35% of the initial radioiodide incorporated into the antiserum. Using a commercially available insulin radioimmunoassay kit, it was determined that iodination did not adversely affect the antirserum's ability to bind insulin.

Following the general procedure given above, iodinations were accomplished using, as the oxidant, more than one bead. As more beads were added to the reaction mixture, the specific activity of the antiserum increased to a maximum of 9.89$\mu$Ci/$\mu$g which was achieved with 6 beads. This represents 99% incorporation of radioiodide into protein and 92% of the original protein was recovered. The addition of more beads did not further increase the specific acitivity, though this can be accomplished by decreasing the amount of antiserum and increasing the amount of Na$^{125}$I employed.

While the oxidant of this invention has been illustrated in connection with the iodination of proteins, it should be appreciated that it has wider applicability. Being an oxidant, it is generally useful in achieving transformations (i.e., chemical changes) in biological specimens where oxidation is necessary. In addition to iodination, another example where this oxidant can find use is in the oxidation of protein sulphydryl groups which is a necessary step when doing protein determinations by the well known Lowry method.

I claim:

1. An oxidant useful in achieving transformations in a biological specimen comprising a water insoluble bead having covalently attached to its surface molecules containing a chloramine group, with the size and shape of said bead being compatible with easy physical separation of the oxidant from a solution of said biological specimen.

2. The oxidant of claim 1 wherein the chloramine group is an N-chloroacrylsulfonamide group, the bead is non-porous, and the oxidant has negligible affinity for said biological specimen.

3. The oxidant of claim 2 wherein the bead is spherical and has a diameter of about 0.01 inch to about 0.25 inch.

4. The oxidant of claim 3 wherein the bead is polystyrene.

5. The oxidant of claims 1, 2, 3, or 4 having an oxidizing capacity of at least 1 $\mu$eq/in$^2$ bead surface area.

6. The oxidant of claim 5 having an oxidizing capacity of at least 10 $\mu$eq/in$^2$ of bead surface area.

7. An oxidant useful for mediating the iodination of biological specimens comprising a water insoluble, non-porous bead having covalently attached to its surface molecules containing a N-chloroarysulfonamide group, said oxidant having a determinable oxidizing capacity and negligible affinity for the biological specimen to be iodinated with the size and shape of said bead being reproducible and compatible with easy separation of the oxidant from a solution of said biological specimen.

8. The oxidant of claim 7 wherein the N-chloroarylsulfonamide groups are N-chlorobenzenesulfonamide groups.

9. The oxidant of claim 8 wherein the bead is polystyrene, is spherical, and has a diameter of about 0.01 inch to about 0.25 inch.

10. The oxidant of claims 7, 8, or 9 having an oxidizing capacity of at least 1 $\mu$eq/in$^2$ of bead surface area.

11. The oxidant of claim 10 having an oxidizing capacity of at least 10 $\mu$eq/in$^2$ of bead surface area.

12. In the process of iodinating a biological specimen comprising iodinating the specimen in the presence of an oxidant and then separating the iodinated specimen from the oxidant; the improvement wherein the oxidant is that described in claim 5.

13. In the process of iodinating a biological specimen comprising iodinating the specimen in the presence of an oxidant and then separating the iodinated specimen from the oxidant; the improvement wherein the oxidant is that described in claim 10.

* * * * *